(12) United States Patent
Brady et al.

(10) Patent No.: US 8,350,581 B1
(45) Date of Patent: Jan. 8, 2013

(54) NONDESTRUCTIVE INSPECTION TO QUANTIFY DEGRADATION OF CYLINDRICAL OBJECTS MADE OF POLYMER MATERIALS

(75) Inventors: Steven K. Brady, Renton, WA (US);
Selina Brownridge, Creve Coeur, MO (US); Donald D. Palmer, Jr., Ballwin, MO (US)

(73) Assignee: The Boeing Company, Chicago, IL (US)

( * ) Notice: Subject to any disclaimer, the term of this patent is extended or adjusted under 35 U.S.C. 154(b) by 538 days.

(21) Appl. No.: 12/583,972

(22) Filed: Aug. 27, 2009

(51) Int. Cl.
*G01R 27/26* (2006.01)

(52) U.S. Cl. ...................................... 324/658

(58) Field of Classification Search ........... 324/658–690
See application file for complete search history.

(56) References Cited

U.S. PATENT DOCUMENTS

| | | | | |
|---|---|---|---|---|
| 6,076,407 | A * | 6/2000 | Levesque et al. | 73/623 |
| 6,657,429 | B1 * | 12/2003 | Goldfine et al. | 324/232 |
| 7,289,913 | B2 * | 10/2007 | Schlicker et al. | 702/38 |
| 7,605,593 | B2 | 10/2009 | Brady | |
| 7,755,351 | B2 | 7/2010 | Brady | |
| 2008/0059082 | A1 | 3/2008 | Morrison | |
| 2008/0169828 | A1 * | 7/2008 | Brady | 324/675 |
| 2008/0174306 | A1 * | 7/2008 | Brady | 324/222 |

OTHER PUBLICATIONS

Society of Plastics Engineers, Polymers (Resins), available at http://www.4spe.org/plastics-encyclopedia/polymers-resins on Dec. 5, 2011.*
Pethrick, R.A. et al; Use of High and Low Frequency Dielectric Measurements in the NDE of Adhesively Bonded Composite Joints; Nondestructive Evaluation and Health Monitoring of Aerospace Materials, Composites, and Civil Infrastructure IV; Proc. of SPIE vol. 5767; 2005; pp. 48-58.
Boinard, P. et al.; Novel non-Destructive Technique to Assess the Degradation of Adhesively Bonded Composite Structures; Insight vol. 43 No. 3; Mar. 3, 2001; pp. 159-162.

* cited by examiner

*Primary Examiner* — Melissa Koval
*Assistant Examiner* — Daniel Miller
(74) *Attorney, Agent, or Firm* — Armstrong Teasdale LLP (57) ABSTRACT

Apparatus for non-destructively testing a polymeric cylindrical object to measure aging characteristics includes a source of electrical energy, a monitoring device, a probe for engaging an inner surface of the cylindrical object, and a conductor connecting at least the source of electrical energy and the probe, the probe comprising contact portions having object engaging surfaces including capacitor circuitry thereon. The probe further includes a nose portion having recesses disposed about the circumference within which the contact portions are housed, the nose portion being engagable with an inner surface of the cylindrical object and the object engaging surfaces being movable between a first position in which the object engaging surfaces are housed entirely within recesses and a second position in which the object engaging surfaces are deployed away from the nose portion.

17 Claims, 5 Drawing Sheets

NONDESTRUCTIVE INSPECTION TO QUANTIFY DEGRADATION OF CYLINDRICAL OBJECTS MADE OF POLYMER MATERIALS

FIELD OF THE DISCLOSURE

The present disclosure relates generally to non-destructive testing for measuring degradation of polymer materials, and more particularly to a method and apparatus for measuring, from the inside, degradation of polymer cylindrical objects, such as aircraft fuel lines and hoses.

BACKGROUND OF THE DISCLOSURE

Aircraft hoses and fuel lines are often exposed to chemicals, high heat and other environmental conditions during their lifetimes. Various aging mechanisms cause the hoses and fuel lines to degrade and then to crack and leak, or fail altogether. Some aging mechanisms include rapid changes in environmental temperatures over substantial periods of time, sustained periods of severe vibrations, and exposure to deleterious chemicals and other similar agents.

Various measures have been implemented to prevent fuel line and hose leaks and failures. For example, sections of such components have been extracted and tested in a laboratory environment. But this is counterproductive as it leads to destruction of the components and the necessity then to replace them. Another technique has been to implement maintenance schedules mandating fuel line replacement. Such schedules have been designed to ensure safe operation, especially in aircraft where the hoses and fuel lines are exposed to the harshest environments. As a result, these components in many aircraft are often needlessly replaced according to the schedules even though they still have useful life left in them. Moreover, the replacement maintenance is costly and time consuming.

It would therefore be most desirable if an apparatus and method were available to non-destructively measure the degradation that has occurred in the hoses and fuel lines so that replacement intervals could be established according to need rather than per a schedule. Such a device would drive down maintenance costs and minimize aircraft downtime.

Nondestructive testing techniques employing dielectric spectroscopy and dielectric loss as a measure of polymer aging have been developed to non-destructively inspect the mechanical properties of a polymer material structure, as has been disclosed by R. A. Pethrick, D. Hayward, B. K. McConnell, and R. L. Crane in their paper "Use of high and low frequency dielectric measurements in the NDE of adhesively bonded composite joints", and in the document entitled "Novel non-destructive technique to assess the degradation of adhesively bonded composite structures" authored by P. Boinard R. A. Pethrick, W. M. Banks, and R. L. Crane. However, neither of these techniques have been successfully used in the non-destructive testing of tubes or hoses with polymer inner walls.

Accordingly, there is a need for a method and apparatus for nondestructively measuring the amount of deterioration and remaining useful life of polymeric parts as they experience degradation through aging and exposure to harsh heat or chemical environments. Embodiments of the disclosure are directed toward satisfying this need.

SUMMARY OF THE DISCLOSURE

In one aspect of the disclosure, an apparatus for nondestructively detecting changes in dielectric properties characteristic of aging in polymer materials encompasses a circuit including a capacitive probe that produces an electric field coupled with the material, the probe being engageble with a surface of the material, and an analyzer for analyzing the response of the circuit to changes in the electric field resulting from the detection of aging characteristics in the polymer material. The circuit may be a tuned resonant circuit that includes a first variable inductor for tuning the circuit and a second variable inductor for impedance matching the circuit with the analyzer. The capacitive probe includes first and second sets of substantially coplanar, spaced apart conductors forming a surface capacitor. The first and second sets of substantially coplanar, spaced apart conductors include interlaced conductive fingers formed on a circuit board, and the electric field is generated by surface effects between the conductors. The apparatus further includes a substrate supporting the surface capacitor which is movable into engagement with the part, and may include tightening elements for securing the surface capacitor against the part or, alternatively, a plurality of arms on each of which a surface capacitor is supported that are pivotable into engagement with a surface of the part. The apparatus further includes a driver mechanism for driving the arms outwardly of the housing, and the driver may be pneumatically actuated by pressure or vacuum.

In another aspect of the disclosure, a method of detecting aging characteristics in polymer parts includes the steps of capacitively coupling a tuned resonant circuit with the part by placing the circuit in physical contact with the part, where changes in the resonance of the circuit are indicative of changes of the dielectric constant in the part, and analyzing the changes in the resonance of the tuned circuit. The method may further include steps of applying an RF signal to the tuned circuit, generating an electric field using the RF frequency signal, and penetrating the part with the electric field generated.

In another aspect of the disclosure, an apparatus for nondestructively testing a polymeric cylindrical object to measure aging characteristics includes a source of electrical energy, a monitoring device, a probe for engaging an inner surface of the cylindrical object, the probe bearing capacitor circuitry that will generate an electric field to penetrate the surface of the object when the circuitry is energized, and a conductor connecting at least the source of electrical energy and the capacitor circuitry, the probe including contact portions having object engaging surfaces movable into contact with the inner surface of the object and bearing the capacitor circuitry thereon, the probe further including a nose portion having recesses disposed about the circumference within which the contact portions are housed, the nose portion being engagable with an inner surface of the cylindrical object and the object engaging surfaces being movable between a first position in which the object engaging surfaces are housed entirely within the recesses and a second position in which the object engaging surfaces are deployed away from the nose portion. The capacitor circuitry of the apparatus further includes pairs of oppositely charged electrically conducting elements, and the electric field is generated by surface effects between the oppositely charged elements.

Still another aspect of the disclosure is a method of detecting aging characteristics in polymer parts comprising the steps of (A) capacitively coupling a tuned resonant circuit with the part by placing the circuit in physical contact with the part, wherein changes in the resonance of the tuned circuit are indicative of changes in the dielectric constant of the part, and (B) analyzing the changes in the resonance of the tuned circuit. The method further includes the steps of applying an RF frequency signal to the tuned circuit, generating an electric field using the RF signal, and penetrating the part with the electric field generated.

Further aspects of the apparatus and the method of using the apparatus are disclosed herein. The features as discussed above, as well as other features and advantages of the present disclosure will be appreciated and understood by those skilled in the art from the following detailed description and drawings.

DETAILED DESCRIPTION OF THE DISCLOSURE

Embodiments of the present invention now will be described more fully hereinafter with reference to the accompanying drawing. However, many different embodiments are contemplated and the present disclosure should not be construed as limited to the embodiments set forth herein; rather, these embodiments are provided so that this disclosure will be thorough and complete and better convey the scope of the disclosure to those skilled in the art.

The present disclosure describes an apparatus and a method for determining aging characteristics of the polymeric inner wall of a cylindrical component, such as a fuel line, by measuring changes in the dielectric properties of the polymer. The apparatus of the present disclosure includes a supporting body having a first portion that carries capacitor circuitry and is engagable with the inner wall of a hose or a fuel line, and a second portion that moves the capacitor circuitry into and out of engagement with the inner wall of the cylindrical component.

The method of the present disclosure includes correlating the measured properties with a lookup table of known aging characteristics, and determining when the measured dielectric properties exceed a predetermined threshold value, which would indicate it is time to replace the component.

Figures 1, 2:
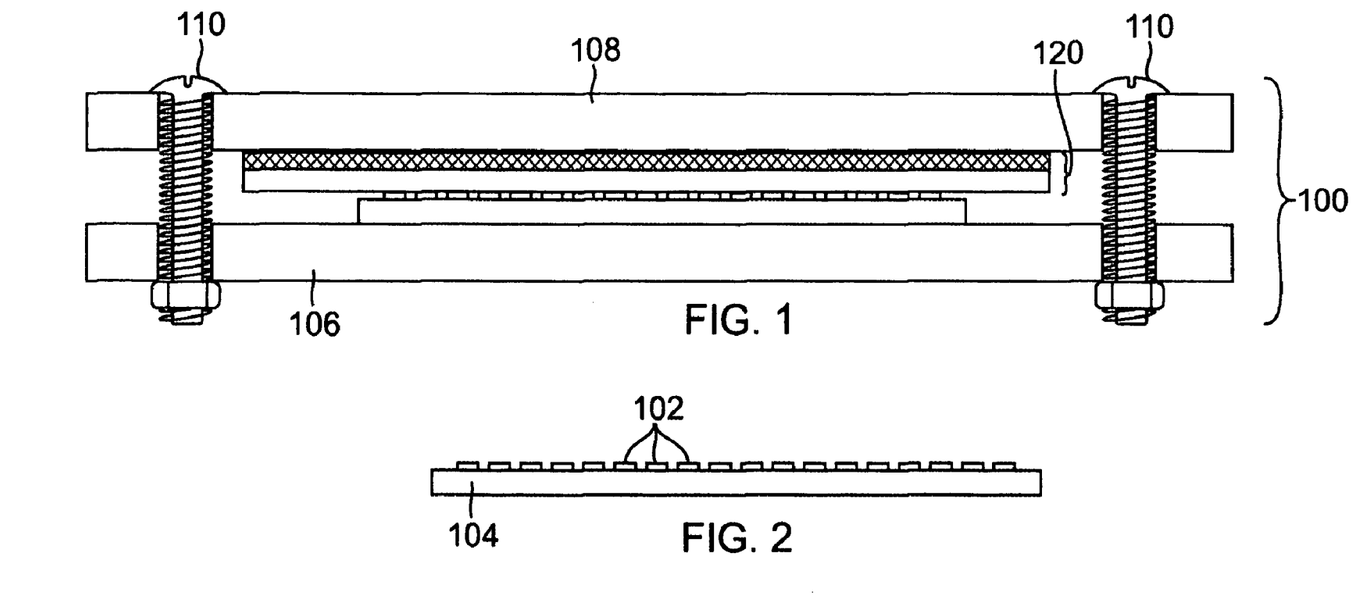
FIG. 1 shows a first embodiment of an apparatus for non-destructively testing a section of cylindrical fuel line in accordance with the present disclosure.
FIG. 2 is a side view of the surface capacitor of the embodiment of FIG. 1.
Figure 3:
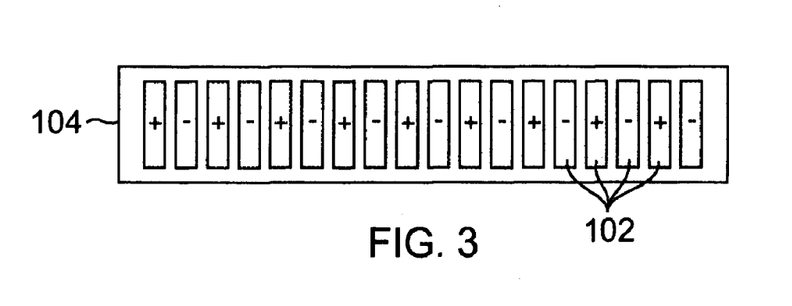
FIG. 3 is a top view of the surface capacitor of the embodiment of FIG. 1.

Referring now to FIGS. 1-3, a first embodiment of the test apparatus 100 includes capacitor circuitry 102 (shown in particular in FIGS. 2 and 3) carried on an insulating supporting member 104, as for example a circuit board. The circuitry consists of pairs of side-by-side, spaced apart, regions of oppositely charged conductive material, each pair of conductive material regions including a positively charged region and a negatively charged region. The circuitry is mounted to a first metal plate 106, which is arranged in parallel spaced relationship with a second metal plate 108 that aids in clamping and aligning the first plate 106 and its circuitry with the fuel line section 120. The conductive regions on the first plate face the second plate, and the two plates are held together in spaced apart relationship by threaded fasteners 110 that pass through aligned apertures in the two plates. The bore of the apertures can be threaded to match the threading of the fasteners 110, or the fasteners 110 can be provided with bolts (not shown) that can be threaded onto the shaft of the fasteners 110 and rotated in such a manner that they are moved in a direction toward, and tightened against, the second plate 106.

In using the first embodiment of the test apparatus, a section 120 of a fuel line can be positioned between the two plates 106, 108 with the conductive regions on the first plate being placed in juxtaposition with the inner surface of the fuel line section and the capacitor circuitry being forced into tight engagement with the inner surface of the fuel line section using the threaded fasteners. Electronics carried by the apparatus provides the circuitry with electrical energy and the signal information obtained is evaluated.

Figure 4:
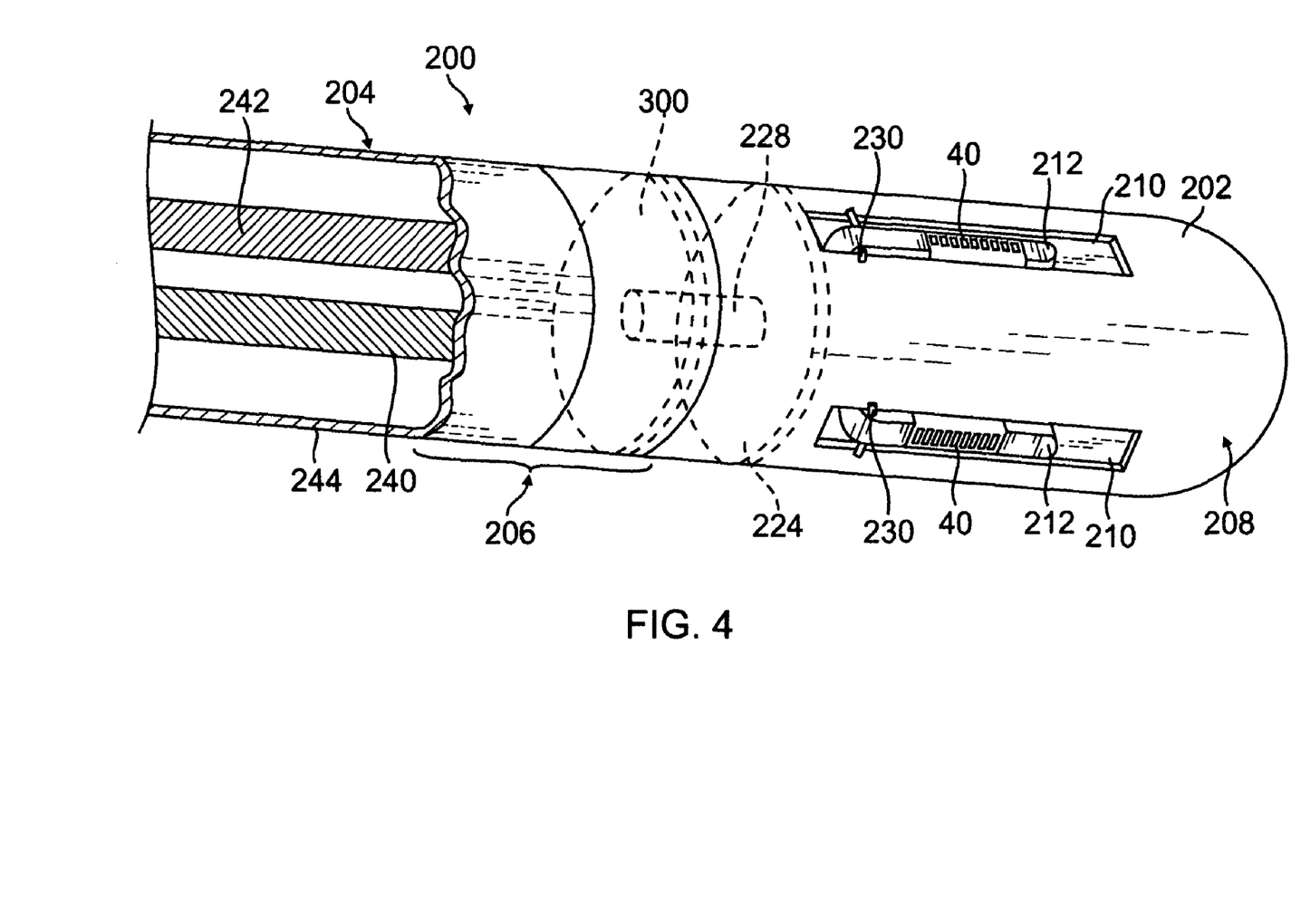
FIG. 4 shows a second embodiment of apparatus for non-destructively testing the polymer inner wall of a tube or hose in accordance with the present disclosure.
Figure 5:
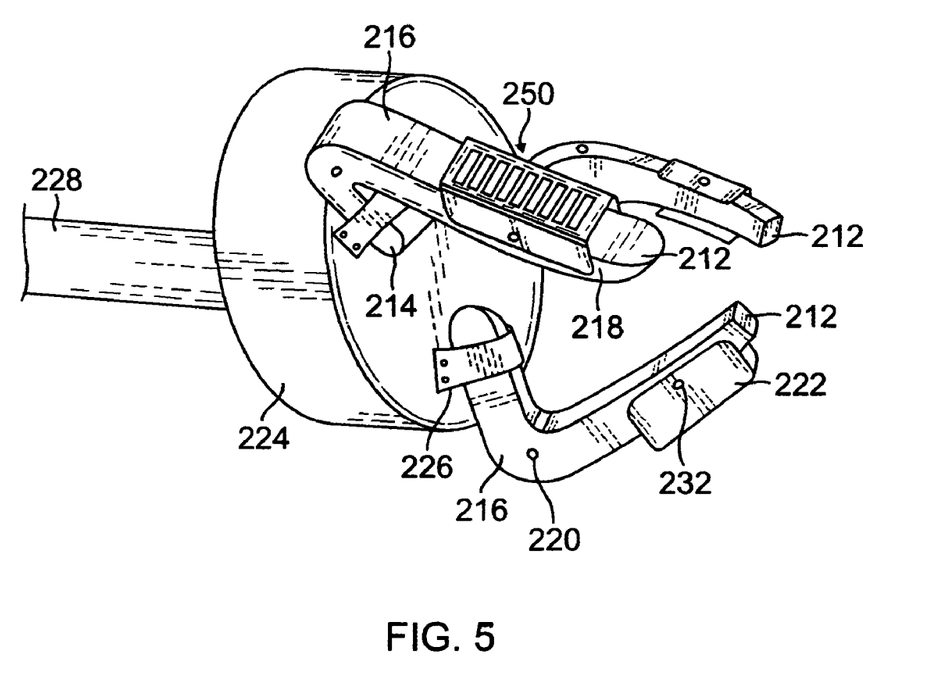
FIG. 5 is a close up view of the capacitor finger assembly contained in the NDT apparatus shown in FIG. 4.

A second embodiment 200 of the test apparatus is shown in FIGS. 4 and 5, and includes a cylindrical housing 202 having a conduit section 204, a central section 206, and a nose section 208 that is inserted into a fuel line or other cylindrical member to be evaluated. The nose portion includes a plurality of recesses 210 extending longitudinally about the circumference in which fingers 212 are housed. Preferably, the recesses number at least two.

As seen in FIG. 5, the fingers 212 each include a foot portion 214, a knee portion 216, and a forward portion 218 on which the capacitor circuitry is mounted. The knee portion includes an aperture 220 extending therethrough. The capacitor circuitry 250 is either carried directly on, or on a plate 222 pivotably carried on, the forward portion of the fingers 218. The foot portion of each finger 212 is secured to a disc 224 by a fastener 226. The disc 224 (also shown in phantom in FIG. 4) is mounted on a rod 228 that extends rearwardly toward the central section 206 where the rod is attached to a driver 300 (shown in phantom in FIG. 4), housed in the central section 206 of the housing 202. It is contemplated that the driver can be a second disc (for example, a piston) which is pneumatically reversibly movable in the central section, or a diaphragm which is reversibly pneumatically movable in the central section. Positioned at the rearward end of each recess 210 of the nose portion and attached to the nose portion is a pivot pin 230. Each pivot pin extends through the aperture in the knee portion 216 of a respective one of the fingers The pivot pins constrain the fingers to pivoting motion into and out of the recesses in response to movement of the driver in a rearward direction and in a forward direction, respectively.

As mentioned above, the capacitor circuitry can be carried directly on an outer surface of the finger at the finger forward region. Alternatively, the capacitor circuitry can be carried on a plate 222 pivotally mounted to the forward region of each of the fingers. As shown in FIG. 5, each plate is pivotally secured to its respective finger by a pivot pin 232.

Housed within the conduit portion of the cylindrical housing is an electrical conductor 240 and a pneumatic conduit 242, the latter being pneumatically coupled with the driver 300 (it is to be understood that the term "pneumatic" encompasses positive pressure, or negative pressure (e.g., vacuum), in the conduit 242). The driver 300 is moved in response to operation of the pneumatic source. Thus, when the source exerts positive pressure on the driver 300, it moves forwardly so that the fingers are forced from a first position (shown in FIG. 4) in which they are housed, each substantially entirely within a respective one of the recesses in the supporting member, to a second position in which they are extending radially outwardly of the casing 202 and in secure engagement with the inner wall of the fuel line. When it is desired to disengage the fingers from the inner wall of the fuel line, the pressure is released and the fingers move back to their first position in the recesses so that the capacitor circuitry is once again housed within the recesses. In this way, the capacitor circuitry on the forward portion of the fingers can be forced against the inner wall of the fuel line and then retracted. The pivoting plates 222 on the portions of the fingers where the capacitor circuitry is mounted accommodate any irregularities in the contour of the inner surface of the fuel line.

Figure 7:
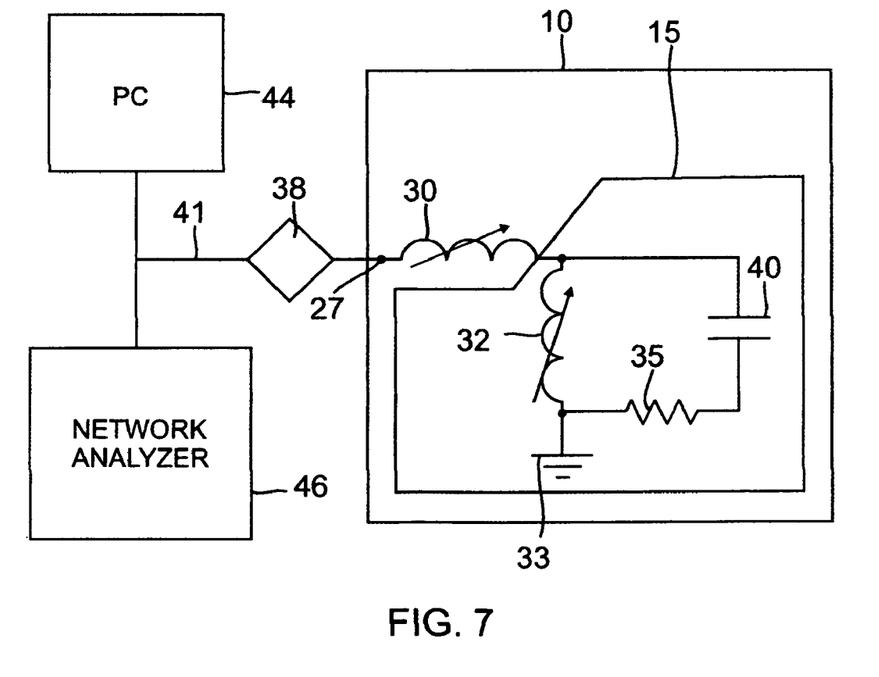
FIG. 7 is a simplified block and schematic illustration of an electrical circuit forming part of the apparatus.

The central section of the apparatus also includes an electronic circuit which provides an interface between the contacts on the fingers and an analytical device for processing the signal information obtained during operation of the probe, such as a network analyzer (see for example the exemplary circuit shown in FIG. 7).

The conduit section 204 is covered with a coiled or braided cover 244 that surrounds the conductor (eg, a coaxial cable) and the pneumatic conduit (eg, an air or vacuum hose).

Figure 6:
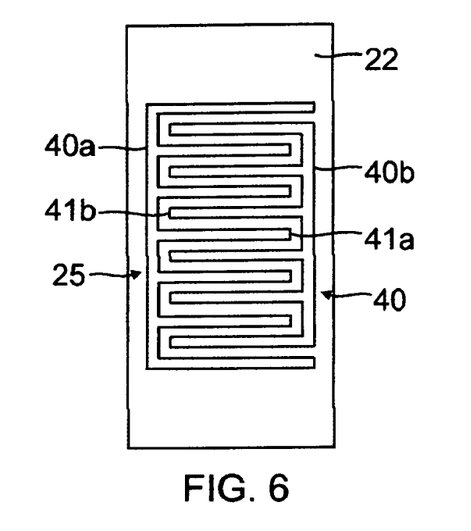
FIG. 6 is a plan illustration of a capacitor circuit carried by the embodiments of the NDT apparatus shown in FIGS. 1-5.

FIG. 6 is a top view looking down on a surface of one of the plurality of fingers that engages with the inner wall of the fuel line, and shows a conductor configuration of the capacitor circuitry carried by the outer surface of the probe finger that abuts against the inner wall of the fuel line tube. The surface capacitor comprises first and second sets of interlaced conductive elements 40a, 40b which are spaced slightly from each other and lie in a plane. The surface capacitor is preferably covered with a thin protective layer of material, such as plastic or glass, which allows transmission therethrough of an electric field. Alternatively, the thin protective layer could take the form of an insulating film.

FIG. 7 depicts an example of electronic circuitry carried by the test apparatus and its functional connection with a network analyzer. This circuitry is disclosed in co-pending US patent application 2008/0169828 (assigned to the same assignee of the present application and incorporated herein by reference), and is described as follows. The capacitor circuitry carried the test apparatus is shown at 40 in both FIGS. 6 and 7. The inherent resistance of tuning inductor 32 and surface capacitor 40 is represented as a collective resistance 35 shown in the FIG. 7 circuit. The tuning inductor 32, surface capacitor 40, and collective resistance 35 form an LRC resonant circuit 15. The variable tuning inductor 32 allows the circuit 15 to be tuned to a particular resonant frequency. The variable coupling inductor 30 (which could also be a variable capacitor) allows the circuit 15 to be impedance-matched to the network analyzer 46. The test apparatus (100, 200) is connected through the connector 38 and coaxial cable 41 to the network analyzer and optionally to a personal computer 44 or other computing device.

The network analyzer 46 applies an alternating frequency signal to the circuit 15 and also determines the electrical impedance of the circuit. The alternating signal results in alternating electrical fields being created between the neighboring projections 41a, 41b of the interlaced conductors 40a, 40b of the surface capacitor circuitry 40. The alternating electric fields interact directly with the polymer material that lines the component, that is the tube or hose being inspected. The frequency of the signal applied to the circuit 15 by the network analyzer is, preferably, between 1 MHz and 100 MHz. This range of frequency has been found to be best for inspecting polymer fuel lines.

When using the test apparatus of the disclosure, the capacitor circuitry is placed in contact with the polymer such that the electric field lines penetrate the polymer. This contact occurs in a repeatable manner with either the pressing of the capacitive circuitry of the first embodiment against the polymer, or by movement of the fingers of the second embodiment radially outwardly toward the inner surface of the polymer component.

Some polymer components also contain conducting elements. An example is carbon fiber reinforced polymer (CFRP) composites, where the carbon fibers are conductive. It has been found that such samples can support the flow of eddy currents induced into the sample magnetically. In such cases, the polymer is naturally incorporated as a capacitive dielectric in the effective circuit which supports eddy currents within the material.

The probe of the apparatus comprises a tuned resonant circuit, tuned to resonate at a predetermined frequency. The probe may be driven and interrogated by a network analyzer, for example. An absorption curve for the probe is returned in a narrow band about the predetermined frequency. From one sample to the next, this curve will have differing magnitude and phase values at all measured frequency points correlated to differences in the degradation state of the samples. The precise measuring of the absorption curve, and then analysis of the corresponding data, comprises the measurement. Analysis of the data comes by comparison with similar curves recorded from "standards" samples aged in a controlled way to various degradation states of interest.

In other words, degradation of the polymer changes its dielectric properties. By means of the present disclosure, the dielectric is coupled with the capacitive element (C) of a resonant LCR circuit, where L is inductance and R is resistance. The changing dielectric changes C, which changes the resonance characteristics of the LCR circuit. These changes comprise the data our invention measures to determine a polymer's state of health.

On the other hand, broad band data acquisition does not rely on a resonant circuit incorporating the capacitive element of the disclosure. In broad band operation, the dielectric values (dielectric constant c, and dielectric dissipation) of the polymer of interest are just measured using a LCR meter, for example, coupled with knowledge of the geometry and contact parameters of the probe. This can be done at any frequencies of interest, but preferably at frequencies from 1 to 100 MHz.

Use of the apparatus of the present disclosure necessitates the development of acceptance criteria for polymer-based materials. This requires establishing correlations between the nondestructive measurements and performance-based data obtained by destructive testing of some sort. In the case of polymer-based components, such as fuel lines, pressure testing and Shore A hardness testing are the two methods commonly used.

Figure 8:
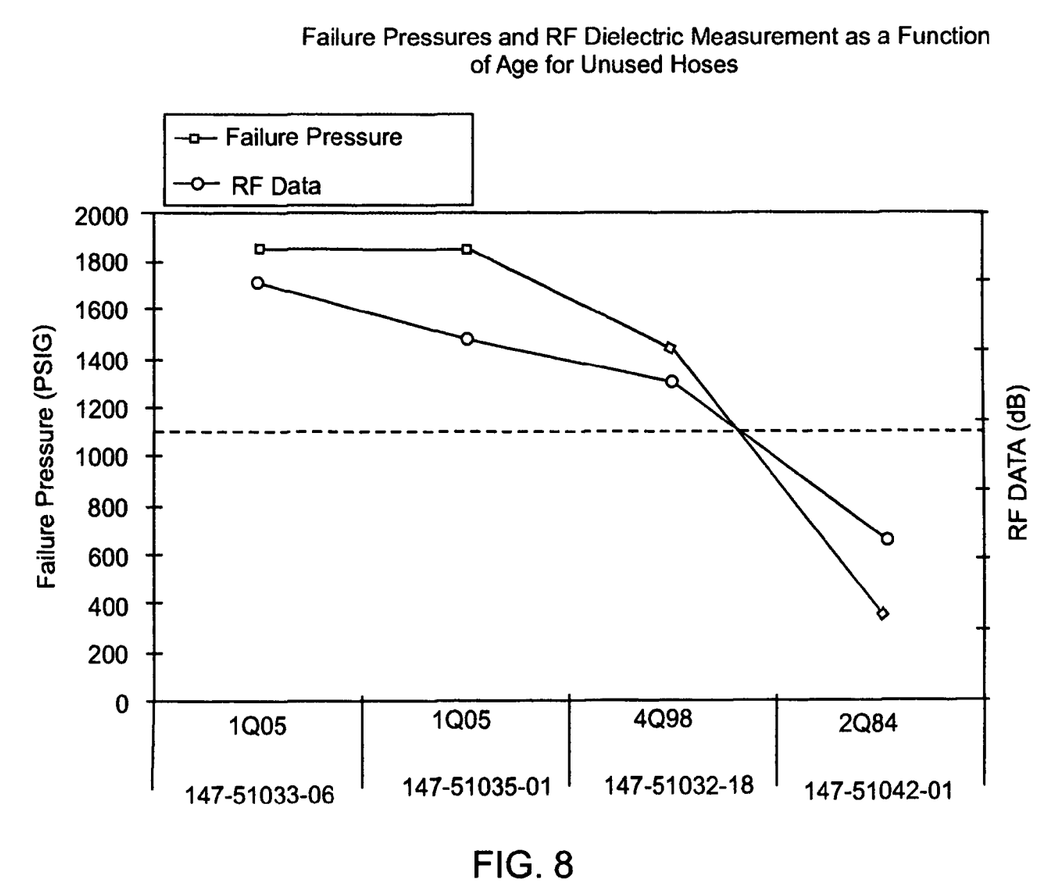
FIG. 8 is a graph useful in determining threshold values representing material deterioration.

The graph in FIG. 8 shows failure pressure, along with RF dielectric measurement data collected using an RF (Radio Frequency) technique. Both values are plotted against age of fuel line test specimens. The dashed horizontal line in the Figure represents the lowest allowable failure pressure (determined hypothetically). The failure pressure lower limit is then cross-referenced with the corresponding RF dielectric data. For example, the RF dielectric data might be 5.6 db in the case of one polymer-based material system. Any dielectric value below 5.6 db would then correspond to failure pressures below the lowest design limit (shown in FIG. 8 at 1100 PSIG). The 5.6 db value would then become the acceptance criteria (represented by the dashed line). This would allow the components to be tested non-destructively to determine if the parts are still safe to use on the aircraft without having to perform some type of destructive testing.

With a correlation between nondestructive and destructive measurements having been determined and the nondestructive acceptance criteria defined, inspections can then be performed on in-service components. Those components that fall above the criteria defined may remain in-service, whereas those that fall below should be removed from the aircraft and replaced. For those components that remain on the aircraft, the results of the measurements may also be used as an indicator of remaining life.

While the disclosure has been made with reference to a preferred embodiment, it will be understood by those skilled in the art that various changes may be made and equivalents may be substituted for elements thereof without departing from the scope of this disclosure. Many modifications can be made to adapt a particular situation or material to the teachings of the disclosure without departing from the essential scope thereof. Therefore, it is intended that this disclosure not be limited to the particular embodiment disclosed as the best mode contemplated for carrying out this invention, but that the disclosure will include all embodiments falling within the scope of the appended claims.

The invention claimed is:

1. Apparatus for detecting changes in dielectric properties characteristic of aging in a polymer material having a cylindrical shape, comprising:
    a circuit comprising a capacitive probe configured to produce an electric field coupled with the polymer material, said capacitive probe engageable with a cylindrical inner-surface of the polymer material and comprising:
        a housing;
        at least one arm comprising a foot portion, an arcuate knee portion, and a forward portion, wherein said foot portion, said knee portion and said forward portion are integrally formed, wherein said at least one arm is pivotably mounted to said housing by a pivot in extending through an aperture of said knee portion, wherein said foot portion of said at least one arm is moveable in a first direction to move the corresponding forward portion from a first position in which said forward portion is fully contained within said housing to a second position in which said forward portion is radially displaced from said housing, and wherein said foot portion of said at least one arm is moveable in a second direction to move the corresponding forward portion from said second position to said first position; and
        a surface capacitor mounted to said forward portion; and
    an analyzer configured to analyze a response of said circuit to changes in the electric field resulting from the detection of aging characteristics in the polymer material.

2. The apparatus of claim 1, wherein said circuit is a tuned resonant circuit.

3. The apparatus of claim 2, wherein said tuned resonant circuit comprises a first variable inductor configured to tune the resonant circuit, and a second variable inductor for impedance matching said circuit with said analyzer.

4. The apparatus of claim 1, wherein said capacitive probe comprises first and second sets of substantially coplanar, spaced apart conductors forming said surface capacitor.

5. The apparatus of claim 4, wherein said first and second sets of conductors each comprise interlaced conductive fingers.

6. The apparatus of claim 4, further comprising a circuit board, and wherein said first and second sets of conductors are formed on said circuit board.

7. The apparatus of claim 1, wherein said surface capacitor comprises a set of interlaced electrical conductors and the electric field is generated by surface effects between said conductors.

8. The apparatus of claim 1, wherein said capacitive probe comprises:
    a substrate supporting said surface capacitor and movable into engagement with the polymer material; and
    tightening means configured to secure said surface capacitor against the polymer material.

9. The apparatus of claim 8, wherein said surface capacitor is movable into engagement with a surface of the polymer material.

10. The apparatus of claim 9, wherein said at least one arm comprises a plurality of arms.

11. The apparatus of claim 10, and further comprising a driver mechanism in said housing for driving said arms radially outwardly of said housing.

12. The apparatus of claim 11, wherein said driver mechanism is configured to be pneumatically actuated by pressure.

13. The apparatus of claim 11, wherein said driver mechanism is configured to be pneumatically actuated by vacuum.

14. A method of detecting aging characteristics of a polymer part having a cylindrical opening therein, comprising:
    inserting a housing comprising at least one tuned resonant circuit and a corresponding at least one arm into said cylindrical opening, wherein said at least one arm comprises a foot portion, an arcuate knee portion and a forward portion, wherein said at least one tuned resonant circuit is mounted to said forward portion of said corresponding at least one arm, wherein said foot portion, said knee portion and said forward portion are integrally formed, wherein said at least one arm is pivotably mounted to said housing by a pivot pin extending through an aperture of said knee portion, wherein said foot portion of said at least one arm is moveable in a first direction to move the corresponding forward portion from a first position in which said forward portion is fully contained within said housing to a second position in which said forward portion is radially displaced from said housing, and wherein said foot portion of said at least one arm is moveable in a second direction to move the corresponding forward portion from said second position to said first position;
    capacitively coupling said at least one tuned resonant circuit with a cylindrical inner-surface of the polymer part by moving said forward portion of said at least one arm from the first position to the second position to place the tuned resonant circuit in physical contact with the inner-surface, wherein changes in the resonance of the tuned resonant circuit are indicative of changes in the dielectric constant of the polymer part;
    analyzing the changes in the resonance of the tuned resonant circuit; and
    moving said forward portion of said at least one arm from said second position to said first position and removing said housing from said cylindrical opening.

15. The method of claim 14, further comprising:
    applying an RF frequency signal to the tuned circuit;
    generating an electric field using the RF signal; and
    penetrating the polymer part with the electric field generated.

16. Apparatus for non-destructively testing a polymeric cylindrical object to measure aging characteristics, comprising:
    a source of electrical energy;
    a monitoring device;

a probe for engaging a cylindrical inner-surface of the cylindrical object, said probe comprising capacitor circuitry configured to generate an electric field to penetrate the inner-surface of the object when the said capacitor circuitry is energized;

a conductor connecting at least said source of electrical energy and the capacitor circuitry, said probe comprising contact portions having object engaging surfaces movable into contact with the inner-surface of the object and bearing the capacitor circuitry thereon, said probe further comprising a nose portion having recesses disposed about a circumference of the nose portion within which said contact portions are housable, said nose portion engagable with the inner-surface of the object, said probe further comprising a plurality of arms each comprising a foot portion, an arcuate knee portion, and a forward portion, wherein said foot portion, said knee portion and said forward portion of each arm are integrally formed, wherein one of said contact portions is mounted to said forward portion of each arm, wherein each arm is pivotably mounted to said nose portion by a pivot pin extending through an aperture of said knee portion, wherein said foot portion of each arm is moveable in a first direction to move the corresponding forward portion from a first position in which said forward portion is fully housed within one of said recesses to a second position in which said forward portion is located outside of said recess and radially displaced from said nose portion, and wherein said foot portion of said at least one arm is moveable in a second direction to move the corresponding forward portion from said second position to said first position.

17. The apparatus of claim 16, wherein the capacitor circuitry comprises pairs of oppositely charged electrical conducting elements, and the electric field is generated by surface effects between the oppositely charged elements.

* * * * *